United States Patent [19]

Koninckx et al.

[11] Patent Number: 5,139,478
[45] Date of Patent: Aug. 18, 1992

[54] GAS INSUFFLATION SYSTEM FOR USE IN ENDOSCOPY AND A SURGICAL ENDOSCOPE THEREFOR

[75] Inventors: Philippe Koninckx, Bierbeek; Eugene Vandermeersch, Sint-Joris-Winge, both of Belgium

[73] Assignee: K.U. Leuven Research & Development, Belgium

[21] Appl. No.: 404,892

[22] Filed: Sep. 8, 1989

Related U.S. Application Data

[63] Continuation of PCT/BE88/000,030

[30] Foreign Application Priority Data

Nov. 11, 1987 [NL] Netherlands .................. 8702698

[51] Int. Cl.⁵ .................. A61M 13/00; A61B 1/12
[52] U.S. Cl. .................. 604/26; 604/23; 128/747
[58] Field of Search .............. 604/26, 23, 248, 32; 128/DIG. 12, 747, 748; 251/207

[56] References Cited

U.S. PATENT DOCUMENTS

| | | | |
|---|---|---|---|
| 2,752,917 | 7/1956 | Moller | 604/26 |
| 3,132,428 | 5/1964 | Haissig et al. | 251/207 |
| 3,982,533 | 9/1976 | Wiest . | |
| 4,036,210 | 7/1977 | Campbell et al. | 604/26 |
| 4,207,887 | 6/1980 | Hiltebrandt et al. | 604/26 |
| 4,464,169 | 8/1984 | Semm | 604/26 |
| 4,598,698 | 7/1986 | Siegmund | 604/26 |
| 4,612,783 | 9/1986 | Mertz | 251/207 |
| 4,676,774 | 6/1987 | Semm et al. | 604/26 |
| 4,735,603 | 4/1988 | Goodson et al. | 604/26 |
| 4,781,698 | 11/1988 | Parren | 604/248 |

FOREIGN PATENT DOCUMENTS

| | | |
|---|---|---|
| 3000218 | 7/1981 | Fed. Rep. of Germany . |
| 3209444 | 10/1982 | Fed. Rep. of Germany . |
| 3611018 | 6/1987 | Fed. Rep. of Germany . |

OTHER PUBLICATIONS

U.S. Catheter & Instrument, catalogue, p. 5, Copyright 1957.

Primary Examiner—Stephen C. Pellegrino
Assistant Examiner—Ralph A. Lewis
Attorney, Agent, or Firm—Renner, Otto, Boisselle & Sklar

[57] ABSTRACT

An insufflation system which provides continuous insufflation at a pre-set, limited low insufflation gas pressure and a high insufflation gas flow, thereby avoiding the necessity of measuring the intra-abdominal pressure while insuring that a determined pre-adjustable maximum insufflation gas pressure cannot be exceeded. The system comprises a gas delivery line having an inlet end coupled to a source of insufflation gas and an outlet end for connecting to the gas inlet of a surgical laser-equipped endoscope. A pressure adjustment device is connected into the gas delivery line for establishing a maximum insufflation gas flow pressure in the gas delivery line, and a gas exhaust tube that can be introduced into the body cavity provides for exhausting of insufflation gas delivered to the body cavity solely by the gas delivery line via the endoscope.

18 Claims, 1 Drawing Sheet

GAS INSUFFLATION SYSTEM FOR USE IN ENDOSCOPY AND A SURGICAL ENDOSCOPE THEREFOR

This application is a continuation of International Application No. PCT/BE88/0030 filed Nov. 9, 1988 and entitled "Gas Insufflation System For Use In Endoscopy And A Surgical Endoscope Therefor", which application is hereby incorporated herein by reference and which application designated the United States.

The present invention relates to a gas insufflation system for use in endoscopy.

BACKGROUND OF THE INVENTION

Endoscopy is a technique which is widely used in medicine for inspecting the interior of a body cavity through a small opening. For an inspection of the abdominal cavity, the term laparoscopy is used.

For some years endoscopy has no longer been restricted to the inspection of body cavities. Surgical operations are now carried out by means of endoscopy (endoscopic surgery). The possibilities for endoscopic surgery have recently expanded through the use of operative lasers. The effective mechanism of an operative laser consists of the vaporization/coagulation of tissue by means of the laser beams emitted by the laser. The use of a surgical laser is accompanied by the generation of smoke, which is an extreme nuisance in a restricted body cavity. Vision is hindered so seriously that, unless measures are taken, visibility is reduced to nil within a few minutes, the operating time is lengthened and the operative risk is increased.

Known insufflation systems, by which smoke formed inside a body cavity can be removed, have a number of drawbacks. The known insufflation systems are expensive and work with a high starting pressure of the insufflation gas, while insufficient assurance is provided that a specific maximum insufflation gas pressure in the body cavity will not be exceeded.

DE-A-3.000.218 further describes an insufflation system with which intermittent insufflation is performed and the intra-abdominal pressure is measured. Because insufflation takes place with an overpressure relative to the intra-abdominal pressure there remains a risk of excessive intra-abdominal pressure.

SUMMARY OF THE INVENTION

The present invention provides an insufflation system with which continuous insufflation is performed and which works at a pre-set and limited low insufflation gas pressure and with a high insufflation gas flow. It thus becomes unnecessary to measure the intra-abdominal pressure and it is ensured that a determined pre-adjustable maximum insufflation gas pressure cannot be exceeded. Moreover, the insufflation system according to the invention is relatively inexpensive.

The insufflation system according to the invention comprises a gas inlet which is joined by a coupling to a gas source for the insufflation gas; a pressure adjustment unit which is connected via a gas line to the gas inlet and which can be connected via a gas delivery line to a gas inlet of a surgical laser-equipped endoscope, of which the endoscope tube through which the insufflation gas can flow can be introduced into the body cavity; and a gas exhaust which is to be brought into the body cavity and which can be joined by a coupling to a gas suction unit; where the gas inlet, the gas lines, the endoscope inlet and tube, and the gas exhaust all have an intrim flow passage of an internal diameter such that the insufflation gas flow amounts to more than 2 l/min per cm. water column equivalent.

By arranging the pressure adjustment unit in the gas supply side of the insufflation system, it is ensured that the prevailing pressure of the insufflation gas in the body cavity cannot exceed the set initial pressure. Moreover, it is no longer necessary to bring a pressure measuring unit into the body cavity through a separate opening—such as is required according to a known insufflation system—in order to measure the insufflation gas pressure which prevails therein.

For the invention it is not only necessary that the pressure adjustment unit is arranged in the insufflation gas supply side of the system, but moreover that all gas-carrying lines are of a minimum internal diameter such that at a relatively low insufflation gas pressure of 1–60 cm, preferably 1–30 cm, a gas flow can prevail which is sufficient to realize an adequate removal of the smoke which is formed, such as 40 or 20 l/min at 20 or 10 cm. Water column respectively.

At an insufflation gas pressure of 1–60 cm water column and an insufflation gas flow up to 15 l/min, a minimal internal diameter of 7 mm is favourable for the insufflation gas lines.

If a control unit for the gas supply flow is included in the gas supply line to the endoscope, a control unit for the gas discharge flow is included on the gas exhaust, and the control units for the gas supply/discharge flows are connected to a feedback unit for the gas supply flow control unit, the difference between the gas supply flow and the gas discharge flow can be continuously determined. Using this determined differential flow, either the gas supply flow can be adjusted, or an alarm can be given to indicate that the insufflation gas supply or discharge is or has become insufficient.

It is beneficial if a multi-way tap, which switches between a gas flow position for a flow of ≦1 l/min and at least one other gas flow position for a flow of 5–6 l/min, is included in the gas supply line for the endoscope. For the sake of safety, it is advisable to let the insufflation of gas into (for example) the abdominal cavity to take place slowly at first (1 l/min). As a result the risks of reflex cardiovascular reactions as a consequence of an excessively rapid stretching of the peritoneum, and a risk of an air embolism caused by accidental intravascular insufflation are reduced or eliminated. Further, in the second gas flow position, the gas pressure in the body cavity is limited in a completely safe and reliable way, whereby the risks of reduced ventilation resulting from the diaphragm pressure and of an air embolism are reduced or prevented.

The invention further relates to a surgical endoscope provided with an endoscope inlet for insufflation gas and an endoscope tube. If desired, the insufflation gas can be pre-warmed and/or wetted so that a cooling of the rapidly flowing gas or the desiccation of tissue respectively can be avoided.

As the insufflation gas, any gas which is currently used, such as nitrous oxide, air, carbon dioxide, gas with a specific composition, or mixtures thereof, is suitable.

Mentioned and other features of the insufflation system according to the invention will be further illustrated hereinafter by way of example, on the basis of a number of embodiments, and with reference to the annexed drawings.

DETAILED DESCRIPTION

Figure 1:
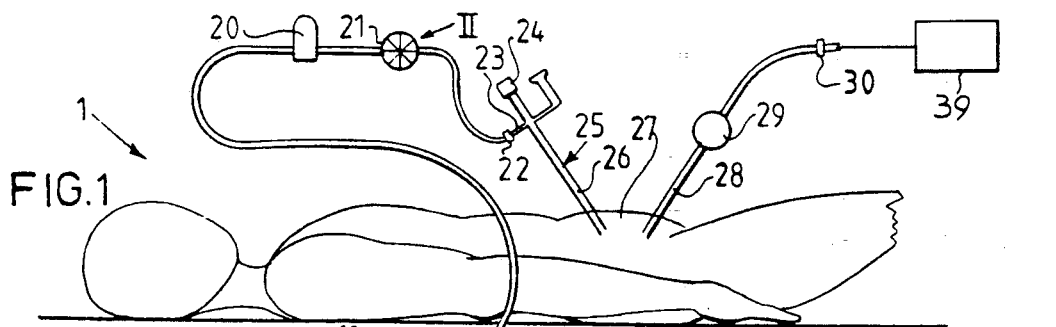
FIG. 1 is an extensively schematized drawing of the usage of a first insufflation system according to the invention.

In the following description, identical components are designated by the same reference numerals.

Although the insufflation systems to be described below relate to laparoscopic laser surgery of the abdominal cavity, it will be apparent that the insufflation system is also applicable to endoscopic laser surgery of other body cavities.

FIG. 1 shows the insufflation system 1 according to the invention, which comprises a gas inlet 2 which is connected through a coupling 3 to a gas bottle 6 which is provided with a stopcock 4 and a pressure reducer 5, and which is filled with a normal insufflation gas and which functions as gas source. The gas inlet 2 is connected via a gas line 7 to a pressure adjustment unit in the form of an air lock 8.

The air lock 8 comprises a stand pipe 11 which is connected to a T-piece 10 and of which the open end 12 is situated at a distance h beneath the surface 13 of the liquid in the vessel 14. The vessel 14 communicates with the atmospheric pressure through an outlet 15.

Further, the stand pipe 11 is sealingly guided through a bearing 16, and the distance h is adjustable with a clamp 18 which is slidable along a standing support 17.

In this manner a maximum insufflation gas pressure can be adjusted in the gas line 7 and in a gas supply line 19.

A flow meter 20 and a multi-way tap 21 are incorporated in succession in the gas supply line 19.

The gas supply line 19 is coupled via a coupling 22 to a gas inlet 23 of a known endoscope 25 provided with a laser 24, of which endoscope the insufflation-gas flowable endoscope tube 26 discharges into the abdominal cavity 27. Accordingly, the gas line 7 and gas supply line 19 function as a gas delivery line for delivering insufflation gas from a source thereof to the gas inlet of the endoscope.

A gas exhaust (or gas exhaust tube) 28, which is further provided with a similar multi-way tap 29, also extends into the abdominal cavity 27. The gas exhaust 28 is connected via a coupling 30 to a gas suction unit, suction apparatus being indicated at 39 in FIG. 1.

Figure 2:
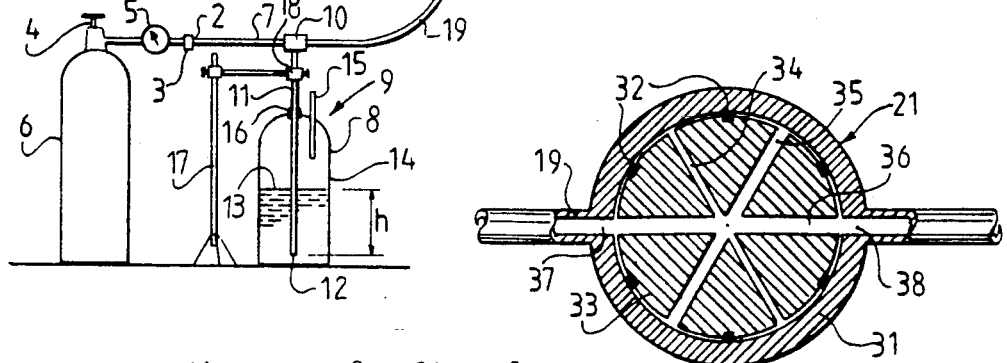
FIG. 2 shows a section on an enlarged scale through a multi-way tap indicated by detail II in FIG. 1.

FIG. 2 shows the multi-way tap 21 or 29 in greater detail. The multi-way tap 21 comprises a housing 31, which is arranged in the gas supply line 19 and in which a tap body 33 is accommodated for rotation by means of bearings 32. The solid tap body 33 is provided with a number of drillings, 34, 35 and 36, which are of increasing diameter and which intersect each other at the centre.

The diameter of the drilling 34 is such that a gas flow of maximally 1 l/min is possible, while the drilling 36 has a diameter (for example 7 mm) such that a gas flow of at least 5-6 l/min is possible. When none of the drillings 34-36 are in line with the tap inlet 37 and the tap outlet 38, the multi-way tap is shut off.

By this means it is simply and quickly possible to set a defined gas flow for a prevailing insufflation gas pressure, as is desired during the initial insufflation and during the laser-surgical operation.

Figure 3:
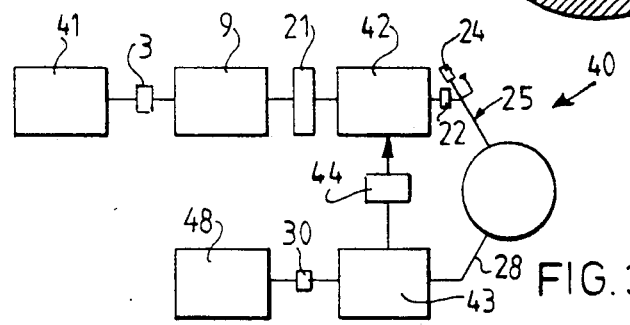
FIGS. 3 to 5 each show a diagram of a different embodiment of the insufflation system according to the invention.

FIG. 3 shows an insufflation system 40 according to the invention. In this system the schematically indicated coupling 3 is connected to a central gas supply 41 of a hospital and the gas exhaust is connected via coupling 30 to a central suction line 48.

A control unit 42 for the gas supply flow is arranged between the multi-way tap 21 and the coupling 22. Further, a control unit 43 for the gas discharge flow is arranged between the exhaust 28 and the coupling 30. Both the control units 42 and 43 are electrically coupled to a control unit 44, which provides feedback to the control unit 42 for the gas supply flow. In other words and according to the above summary of the control units, the control unit 42 functions as a first sensing means for sensing gas supply flow in the gas delivery line, the control unit 43 functions as a second sensing means for sensing gas discharge flow in the gas exhaust tube 28, and the control unit 44 functions as a feedback means for supplying an output signal indicative of the difference between the sensed gas supply and discharge flows. By this means a regulation of the gas supply flow is possible, or alternatively an alarm signal can be given when there is an inadequate gas supply/discharge flow. This alarm signal can discriminate between an inadequate gas supply flow and an inadequate gas discharge flow, and thus communicates the cause of an insufficient smoke removal from the abdominal cavity 27.

Figure 4:
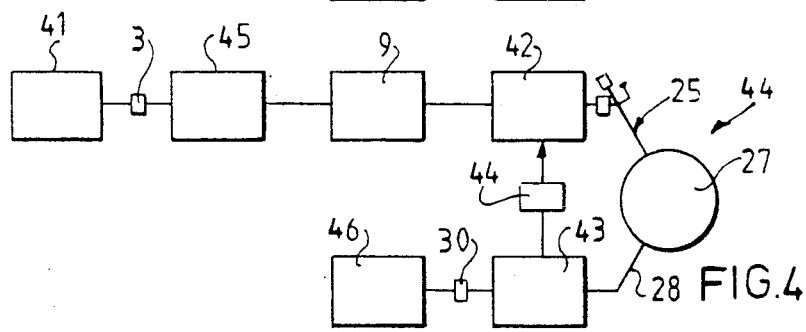

The insufflation system 44 according to FIG. 4 comprises a gas flow adjustment unit 45, whereby the gas flow is continuously adjustable between (for example) 0.5 and 15 l/min, arranged between the coupling 3 and the pressure adjustment unit 9.

The pressure adjustment unit 9 situated downstream with respect to the flow adjustment unit 45 has a range of 1-60 cm. water column. Further, at a gas pressure exceeding 30 cm water column, a special manipulation with a number of steps is necessary, which results in an unintended manipulation being impossible, while in addition a signal gives an regular reminder of this specially adjusted gas pressure. Further, the pressure adjustment unit 9 may consist of a known continuously adjustable pressure limiter with a blowoff valve.

Further, in the insufflation system 44, the exhaust 28 is connected via the coupling 30 to a scavenging system 46 for anaesthesia gases.

Figure 5:
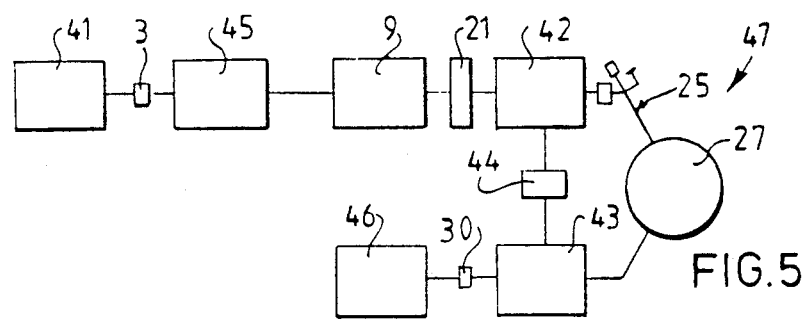

Finally, FIG. 5 shows a last embodiment of the insufflation system 47 according to the invention, in which, unlike the insufflation system 44 shown in FIG. 4, a multi-way tap 21 as according to FIG. 2 is arranged between the pressure adjustment unit 9 and the gas supply flow control unit 42.

In view of the high insufflation gas flow it may be necessary to wetten and/or heat the insufflation gas beforehand in per se known manner.

What is claimed is:

1. An insufflation system, comprising:
    a source of insufflation gas;
    a gas suction unit;
    gas delivery line means for delivering insufflation gas from the source thereof to a gas inlet of a surgical laser-equipped endoscope having an insufflation gas-flowable endoscope tube that can be introduced into a body cavity, said gas delivery line means having at an inlet end thereof means for coupling said inlet end to the source of insufflation gas and at an outlet end thereof means for connecting said outlet end to the gas inlet of the endoscope;

pressure adjustment means connected into said gas delivery line means for limiting the pressure of the insufflation gas flowing in said gas delivery line means to a predetermined maximum insufflation gas flow pressure, and a gas exhaust tube means that can be introduced into the body cavity and that has means for coupling to the gas suction unit for exhausting from the body cavity insufflation gas delivered to the body cavity by said gas delivery line means via the endoscope; and wherein said source of insufflation gas, gas suction unit, gas delivery line means and gas exhaust tube means provide insufflation gas flow in an amount greater than 2 1/min per cm water column for insufflation gas pressure.

2. An insufflation system as claimed in claim 1, wherein said pressure adjustment means and gas delivery line means operate to provide an insufflation gas pressure at the outlet end of the gas delivery line means that is 1-30 cm water column and an insufflation gas flow that is 5-15 1/min.

3. An insufflation system as claimed in claim 1, wherein said gas delivery line means includes between said pressure adjustment means and said outlet end of said gas delivery line means a multi-way tap, which switches between a gas flow position for a flow of greater than 1 1/min and at least one other gas flow position for a flow of 5-6 1/min.

4. An insufflation system as claimed in claim 1, comprising the source of insufflation gas, and wherein said insufflation gas source comprises a central gas supply.

5. An insufflation system as claimed in claim 4, wherein said pressure adjustment means includes an air lock.

6. An insufflation system as claimed in claim 1, wherein said pressure adjustment means includes an air lock.

7. An insufflation system as claimed in claim 1, comprising the gas suction unit, said gas suction unit including a scavenging system for anaesthetic gases connected to said gas exhaust tube means.

8. An insufflation system as claimed in claim 7, wherein said internal diameter of said interior flow passage means is >7 mm.

9. An insufflation system as claimed in claim 1, wherein said internal diameter of said interior flow passage means is >7 mm.

10. An insufflation system as claimed in claim 1, comprising the endoscope, said endoscope including a flow passage for the insufflation gas supplied by said gas delivery line means, said flow passage having an internal diameter for providing insufflation gas flow in an amount greater than 2 1/min per cm water column for the insufflation gas pressure.

11. An insufflation system as claimed in claim 1, comprising the source of insufflation gas, and wherein said insufflation gas source comprises a gas bottle.

12. An insufflation system as claim in claim 1, comprising the gas suction unit, said gas suction unit including a suction apparatus connected to said gas exhaust tube means.

13. An insufflation system as claimed in claim 1, wherein said gas exhaust tube means exhausts from the body cavity insufflation gas delivered to the body cavity solely by said gas delivery line means via the endoscope.

14. An insufflation system, comprising gas delivery line means for delivering insufflation gas from a source thereof to a gas inlet of a surgical laser-equipped endoscope having an insufflation gas-flowable endoscope tube that can be introduced into a body cavity, said gas delivery line means having at an inlet end thereof means for coupling said inlet end to the source of insufflation gas and at an outlet end thereof means for connecting said outlet end to the gas inlet of the endoscope;

pressure adjustment means connected into said gas delivery line means for limiting the pressure of the insufflation gas flowing in said gas delivery line means to a predetermined maximum insufflation gas flow pressure, and a gas exhaust tube means that can be introduced into the body cavity and that has means for coupling to a gas suction unit for exhausting from the body cavity insufflation gas delivered to the body cavity by said gas delivery line means via the endoscope; and wherein said gas delivery line means and gas exhaust tube means have respective interior flow passage means for the insufflation gas of an internal diameter for providing insufflation gas flow in an amount greater than 2 1/min per cm water column for insufflation gas pressure; and comprising first sensing means connected to said gas delivery line means between said pressure adjustment means and said outlet end of said gas delivery line means for sensing gas supply flow in said gas delivery line means, second sensing means connected to said gas exhaust tube means for sensing gas discharge flow in said gas exhaust tube means, feedback means connected to said first and second sensing means for supplying an output signal indicative of the difference between the sensed gas supply and discharge flows, and means responsive to the output signal for regulating gas supply flow.

15. An insufflation system as claimed in claim 14, wherein said gas delivery line means includes between said pressure adjustment means and said first sensing means a multi-way tap, which switches between a gas flow position for a flow of greater than 11/min and at least one other gas flow position for a flow of 5-6 1/min.

16. An insufflation system, comprising gas delivery line means for delivering insufflation gas from a source thereof to a gas inlet of a surgical laser-equipped endoscope having an insufflation gas-flowable endoscope tube that can be introduced into a body cavity, said gas delivery line means having at an inlet end thereof means for coupling said inlet end to the source of insufflation gas and at an outlet end thereof means for connecting said outlet end to the gas inlet of the endoscope;

pressure adjustment means connected into said gas delivery line means for limiting the pressure of the insufflation gas flowing in said gas delivery line means to a predetermined maximum insufflation gas flow pressure, and a gas exhaust tube means that can be introduced into the body cavity and that has means for coupling to a gas suction unit for exhausting from the body cavity insufflation gas delivered to the body cavity by said gas delivery line means via the endoscope; and wherein said gas delivery line means and gas exhaust tube means have respective interior flow passage means for the insufflation gas of an internal diameter for providing insufflation gas flow in an amount greater than 2 1/min per cm water column for insufflation gas pressure, and wherein said pressure adjustment means and gas delivery line means operate to provide an insufflation gas pressure at the outlet end of the gas delivery line means that is 1-30 cm water column and an insufflation gas flow that is 5-15 1/min; and comprising first sensing means connected to said gas delivery line means between said pressure adjustment means and said outlet end of said gas delivery line means for sensing gas supply flow in said gas delivery line means, second sensing means connected to said gas exhaust tube means for sensing gas discharge flow in said gas exhaust tube means, feedback means connected to said first and second sensing means for supplying an output signal indicative of the difference between the sensed gas supply and discharge flows, and means responsive to the output signal for regulating gas supply flow.

17. An insufflation system, comprising gas delivery line means for delivering insufflation gas from a source thereof to a gas inlet of a surgical laser-equipped endoscope having an insufflation gas-flowable endoscope tube that can be introduced into a body cavity, said gas delivery line means having at an inlet end thereof means for coupling said inlet end to the source of insufflation gas and at an outlet end thereof means for connecting said outlet end to the gas inlet of the endoscope:

pressure adjustment means connected into said gas delivery line means for limiting the pressure of the insufflation gas flowing in said gas delivery line means to a predetermined maximum insufflation gas flow pressure, and a gas exhaust tube means that can be introduced into the body cavity and that has means for coupling to a gas suction unit for exhausting from the body cavity insufflation gas delivered to the body cavity by said gas delivery line means via the endoscope; and wherein said gas delivery line means and gas exhaust tube means have respective interior flow passage means for the insufflation gas of an internal diameter for providing insufflation gas flow in an amount greater than 2 1/min per cm water column for insufflation gas pressure; and comprising first sensing means connected to said gas delivery line means between said pressure adjustment means and said outlet end of said gas delivery line means for sensing gas supply flow in said gas delivery line means, second sensing means connected to said gas exhaust tube means for sensing gas discharge flow in said gas exhaust tube means. feedback means connected to said first and second sensing means for supplying an output signal indicative of the difference between the sensed gas supply and discharge flows, and means responsive to the output signal for issuing an alarm signal.

18. An insufflation system, comprising gas delivery line means for delivering insufflation gas from a source thereof to a gas inlet of a surgical laser-equipped endoscope having an insufflation gas-flowable endoscope tube that can be introduced into a body cavity, said gas delivery line means having at an inlet end thereof means for coupling said inlet end to the source of insufflation gas and at an outlet end thereof means for connecting said outlet end to the gas inlet of the endoscope;

pressure adjustment means connected into said gas delivery line means for limiting the pressure of the insufflation gas flowing in said gas delivery line means to a predetermined maximum insufflation gas flow pressure, and a gas exhaust tube means that can be introduced into the body cavity and that has means for coupling to a gas suction unit for exhausting from the body cavity insufflation gas delivered to the body cavity by said gas delivery line means via the endoscope; and wherein said gas delivery line means and gas exhaust tube means have respective interior flow passage means for the insufflation gas of an internal diameter for providing insufflation gas flow in an amount greater than 2 1/min per cm water column for insufflation gas pressure, and wherein said pressure adjustment means and gas delivery line means operate to provide an insufflation gas pressure at the outlet end of the gas delivery line means that is 1-30 cm water column and an insufflation gas flow that is 5-15 1/min; and comprising first sensing means connected to said gas delivery line means between said pressure adjustment means and said outlet end of said gas delivery line means for sensing gas supply flow in said gas delivery line means, second sensing means connected to said gas exhaust tube means for sensing gas discharge flow in said gas exhaust tube means, feedback means connected to said first and second sensing means for supplying an output signal indicative of the difference between the sensed gas supply and discharge flow, and means responsive to the output signal for issuing an alarm signal.

* * * * *